United States Patent
Kwon et al.

(10) Patent No.: US 9,580,399 B2
(45) Date of Patent: Feb. 28, 2017

(54) GERANYL FLAVONOID DERIVATIVE WITH IMPROVED WATER SOLUBILITY, A METHOD FOR PREPARING THE SAME, AND A METHOD FOR TREATING CANCER USING THE SAME

(71) Applicant: KOREA RESEARCH INSTITUTE OF BIOSCIENCE AND BIOTECHNOLOGY, Daejeon (KR)

(72) Inventors: Byoung-Mog Kwon, Daejeon (KR); Dong Cho Han, Daejeon (KR); Yoon-Jeong Jeon, Daejeon (KR); Joongku Lee, Daejeon (KR); Sangho Choi, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 14/732,310

(22) Filed: Jun. 5, 2015

(65) Prior Publication Data
US 2016/0060239 A1 Mar. 3, 2016

(30) Foreign Application Priority Data
Aug. 26, 2014 (KR) .......................... 10-2014-0111413

(51) Int. Cl.
*C07D 311/04* (2006.01)
*A61K 31/352* (2006.01)

(52) U.S. Cl.
CPC ........... *C07D 311/04* (2013.01); *A61K 31/352* (2013.01)

(58) Field of Classification Search
CPC .............................. C07D 311/04; A61K 31/352
See application file for complete search history.

(56) References Cited

PUBLICATIONS

McLean et al. Complete 13C and 1H spectral assignments of prenylated flavonoids and a hydroxy fatty acid from the leaves of Caribbean Artocarpus communis. Mag. Res. Chem. 34, 719-722 (1996).*
Wang et al. "STAT3 inhibition, a novel approach to enhancing targeted therapy in human cancers (Review)" *International Journal of Oncology* 41:1181-1191 (2012).
Zhang et al. "Orally bioavailable small-molecule inhibitor of transcription factor Stat3 regresses human breast and lung cancer xenografts" *PNAS* 109(24):9623-9628 (2012).
Jeon et al. "*Artocarpus altilis* (Parkinson) Fosberg Extracts and Geranyl Dihydrochalcone Inhibit STAT3 Activity in Prostate Cancer DU145 Cells" *Phytotherapy Research* 29:749-756 (2015).

* cited by examiner

*Primary Examiner* — Barbara P Badio
*Assistant Examiner* — Sara E Townsley
(74) *Attorney, Agent, or Firm* — Klarquist Sparkman, LLP

(57) ABSTRACT

The present invention relates to a novel geranyl flavonoid derivative with improved water-solubility or a pharmaceutically acceptable salt thereof, a method for preparing the same, and a method for treating cancer using the same. Particularly, the novel geranyl flavonoid derivative of the present invention inhibits the expression of STAT3 target protein by suppressing the phosphorylation of STAT3 (Signal Transducers and Activators of Transcription 3) protein, suggesting that it has cancer cell growth inhibiting effect in various cancer cell lines. Also, the compound of the invention has the effect of reducing the size and weight of a tumor significantly in vivo, so that the geranyl flavonoid derivative or the pharmaceutically acceptable salt thereof can be efficiently used for the treatment of cancer.

9 Claims, 5 Drawing Sheets

GERANYL FLAVONOID DERIVATIVE WITH IMPROVED WATER SOLUBILITY, A METHOD FOR PREPARING THE SAME, AND A METHOD FOR TREATING CANCER USING THE SAME

CROSS REFERENCE TO RELATED APPLICATION

This application claims the benefit of Korean Patent Application No. 10-2014-0111413, filed Aug. 26, 2014. The Korean application is incorporated herein in its entirety.

BACKGROUND OF THE INVENTION

1. Field of the Invention

The present invention relates to a novel geranyl flavonoid derivative with improved water solubility or a pharmaceutically acceptable salt thereof, a method for preparing the same, and a method for treating cancer using the same.

2. Description of the Related Art

As the civilization advances, the incident rate of cancer grows. Accordingly, the development of an anti-cancer agent is the major issue in the field of bioscience and biotechnology. Cancer is the top-most or the second highest cause of death not only in Korea but also in other counties including USA and Japan, and death of cancer takes more than 50% of the total death rate particularly reported from the general hospitals.

Since President Nixon proclaimed war against cancer in 1971, starting with the explanation of the Novel prize winners Varmus and Bishop about the development procedure of cancer mediated by oncogene, the studies on cancer have progressed greatly for the past 40 years, during which cancer specific oncogenes or tumor suppressor genes have been identified. Even though new cancer treating drugs have been developed based on these studies on the functions and mechanisms of such genes, cancer still stays as a big mountain to conquer.

As an effort to conquer cancer, diagnostic methods have been advanced to facilitate the early diagnosis of various cancers. Progress has also been made in the treatment methods including surgical operation, ratio-therapy, chemotherapy, and biological method, etc. The most representative cancer treatment method is the surgical operation. The surgical operation is most effective in increasing survival rate in early stage cancer patients, but is limited to some specific early stage cancers and is limited in operable regions. To overcome these disadvantages, an attempt to establish the target oriented therapy has been actively tried with targeting a cancer specific gene.

A variety of cancer cells have been targeted for chemotherapy so far. However, a real fundamental anti-cancer drug has not been established yet, and only auxiliary drugs or the drugs only functioning to extend life for a little longer have been developed. The above treatment methods are all effective only in the early stage cancer patients or some specific cancers. So, the death of cancer still increases.

The most representative targeted cancer therapeutics being clinically used these days are Gleevec that inhibits the signal transduction, Heceptin (a breast cancer treating agent), Iressa (a lung cancer treating agent), Avastin (a colon cancer treating agent) working to inhibit angiogenesis, Suten (a kidney cancer treating agent), and Crizotinib (a lung cancer treating agent). The problem of these targeted cancer therapeutics is the resistance which is observed within 6~12 months from the administration. To overcome the resistance, a novel drug has been continuously tried and the treatment method using combined drugs is in the center of the recent study.

To increase the treatment efficiency, studies on cancer development and metastasis, cancer cell physiology, and cancer diagnosis and treatment have been actively undergoing along with the attempts to develop not only a general anticancer agent by screening natural extracts but also a specific targeted novel agents such as an angiogenesis inhibitor and a metastasis inhibitor. Particularly, a selective anticancer agent targeting a specific molecule is on the spotlight because it is expected not only to be safer and more efficient in treatment but also to be easily applied to customized medical treatment and combination therapy.

To prevent the resistance against anticancer drugs and to inhibit the cancer recurrence, the focus of the major anticancer studies have been diverted to cancer cell metabolism, micro-environment around cancer cells, cancer stem cell generation and preservation, etc, since 2010.

STAT (Signal Transducers and Activators of Transcription) proteins act as a signaling protein in cytoplasm, which are therefore involved in signal transduction from cell membrane into nucleus and transcriptional regulation. A variety of STATs having the molecular weight of around 87~113 kDa have been reported, which include STAT1, STAT2, STAT3, STAT4, STAT5, and STAT6.

Among these STAT proteins, STAT3 is necessarily activated in most cancers and plays an important role in cancer development and differentiation. In many cases of malignant cancer, STAT3 activation is observed. In metastatic cancers, the continued activation of STAT3 is frequently observed. STAT3 is directly involved in tumor generation, invasion, and metastasis, and displays resistance against cancer cell apoptosis. Therefore, it is regarded as a promising anticancer strategy to screen STAT3 as a target material.

STAT proteins contain SH2 domain that is able to recognize at least one or two phosphotyrosine sequences in cytoplasm of the activated receptor. The SH2 (Src Homology-2) domain plays a role as a phosphorylation-dependent switch that regulates receptor recognition and DNA binding. As a result, STAT proteins can bridge the activation of a cell surface receptor and gene regulation (Darnell, J. E., Proc. Natl. Acad. Sci. (USA), 94:11767-11769 (1997)).

The activation of dormant STAT molecules in cytoplasm of an animal cell is achieved by the cytokine surface receptor and the growth factor receptor which is noncovalently linked to the cykine surface receptor and has Jak kinase activity or tyrosine kinase activity.

The binding between the ligand and the cell surface induces phosphorylation of tyrosine in cytoplasm of the receptor, resulting in the preparation of the STAT SH2 domain binding site. The binding with STAT on the surface of the receptor induces phosphorylation of tyrosine by Jak or receptor kinase. The phosphorylated STAT protein forms SH2 domain mediated dimer, which moves into the nucleus. In the inside of the nucleus, the dimer binds with DNA to induce transcription of a specific gene. The STAT protein signal transduction system can be stopped by dephosphorylation and protein decomposition.

Researchers have recognized the activated form of STAT in various cancers. In particular, STAT3 was identified to be activated not only in blood cancer such as leukemia but also in solid cancer such as breast cancer, head & neck cancer, melanoma, ovarian cancer, lung cancer, pancreatic cancer, and prostate cancer, suggesting that it could be an important target of anticancer study [Hua Yu and Richard Jove, Nature Review Cancer (2004), 8, 945]. Therefore, the inhibition of STAT protein leads to tumor control via combined anticancer mechanisms of apoptosis, anti-angiogenesis, and blocking immune evasion, etc. So, the inhibition of STAT protein is important as an efficient and practical technical resource for the development of an anticancer drug. And the resultant anticancer agent is expected to be more efficient in treating cancer than the conventional anticancer agents displaying linear action.

The present inventors tried to develop a novel compound exhibiting inhibitory effect on the activity of STAT3 protein. As a result, the inventors found out that the newly synthesized geranyl flavonoid derivative inhibited the expression of STAT3 target protein by inhibiting the phosphorylation of STAT3 protein so that it could bring the cancer cell growth inhibition effect in various cancer cell lines. The present inventors also confirmed that the novel geranyl flavonoid derivative inhibited the increase of the size and weight of a tumor significantly in the prostate cancer mouse model, suggesting that the novel geranyl flavonoid derivative or the pharmaceutically acceptable salts thereof and the preparation method of the same could be efficiently used for treating cancer, leading to the completion of the present invention.

SUMMARY OF THE INVENTION

It is an object of the present invention to provide a novel geranyl flavonoid derivative with improved water solubility or a pharmaceutically acceptable salt thereof, and a method for preparing the same, and a method for treating cancer using the same.

To achieve the above object, the present invention provides the geranyl flavonoid derivative represented by the below formula 1 or the pharmaceutically acceptable salt thereof.

[Formula 1]

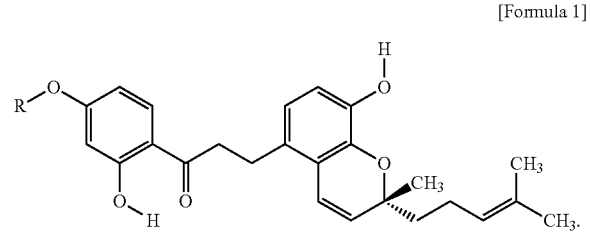

Wherein,
R is a $C_{1-3}$ linear or branched chain alkoxy group;
a $C_{1-4}$ linear or branched chain alkyl carbonyl group;
a substituted or unsubstituted 6-membered heterocycloalkyl carbonyl group comprising one or two heteroatoms selected from the group consisting of O and N;
a substituted or unsubstituted $C_{4-10}$ heteroaryl comprising one or more Ns;
a substituted or unsubstituted $C_{6-10}$ aryl sulfonyl; or
a dimethylamino $C_{1-3}$ linear or branched chain alkyl, Wherein the substituted 6 membered heterocycloalkyl, substituted $C_{4-10}$ heteroaryl and substituted $C_{6-10}$ aryl may be independently substituted by one or more $C_{1-4}$ linear or branched alkyl.

The present invention also provides a method for preparing the flavonoid derivative of claim 1 containing the step of preparing a geranyl flavonoid derivative by reacting hydroxy geranyl flavonoid (4), in the presence of a reaction solvent, with dimethyl aminoethyl chloride (5) substituted in the presence of a carbonate compound.

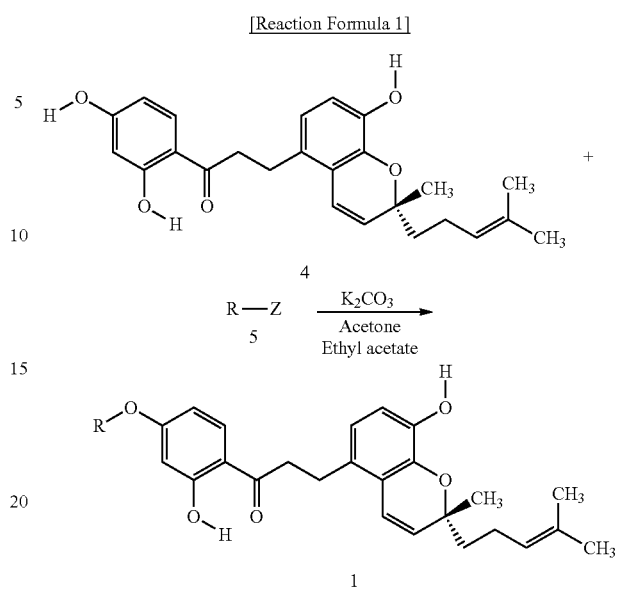

(In the reaction formula 1, R is as defined in formula 1; and Z is the leaving group.)

The present invention further provides a method for treating cancer containing the step of administering a pharmaceutically effective dose of the geranyl flavonoid derivative represented by formula 1 or the pharmaceutically acceptable salt thereof.

Advantageous Effect

The novel geranyl flavonoid derivative of the present invention inhibits the expression of STAT3 target protein by inhibiting the phosphorylation of STAT3 (Signal Transducers and Activators of Transcription 3) protein, and accordingly the derivative displays cancer growth inhibition effect in various cancer cell lines, precisely by inhibiting the size and weight of a tumor significantly in vivo. Therefore, the geranyl flavonoid derivative of the present invention can be efficiently used for a method for treating cancer.

BRIEF DESCRIPTION OF THE DRAWINGS

The application of the preferred embodiments of the present invention is best understood with reference to the accompanying drawings, wherein:

FIG. 1a is a diagram illustrating the hydrogen NMR spectrum of CG-901-1. FIG. 1b is a diagram illustrating the hydrogen NMR spectrum of CG-901-2.

DESCRIPTION OF THE PREFERRED EMBODIMENTS

Figure 1A:
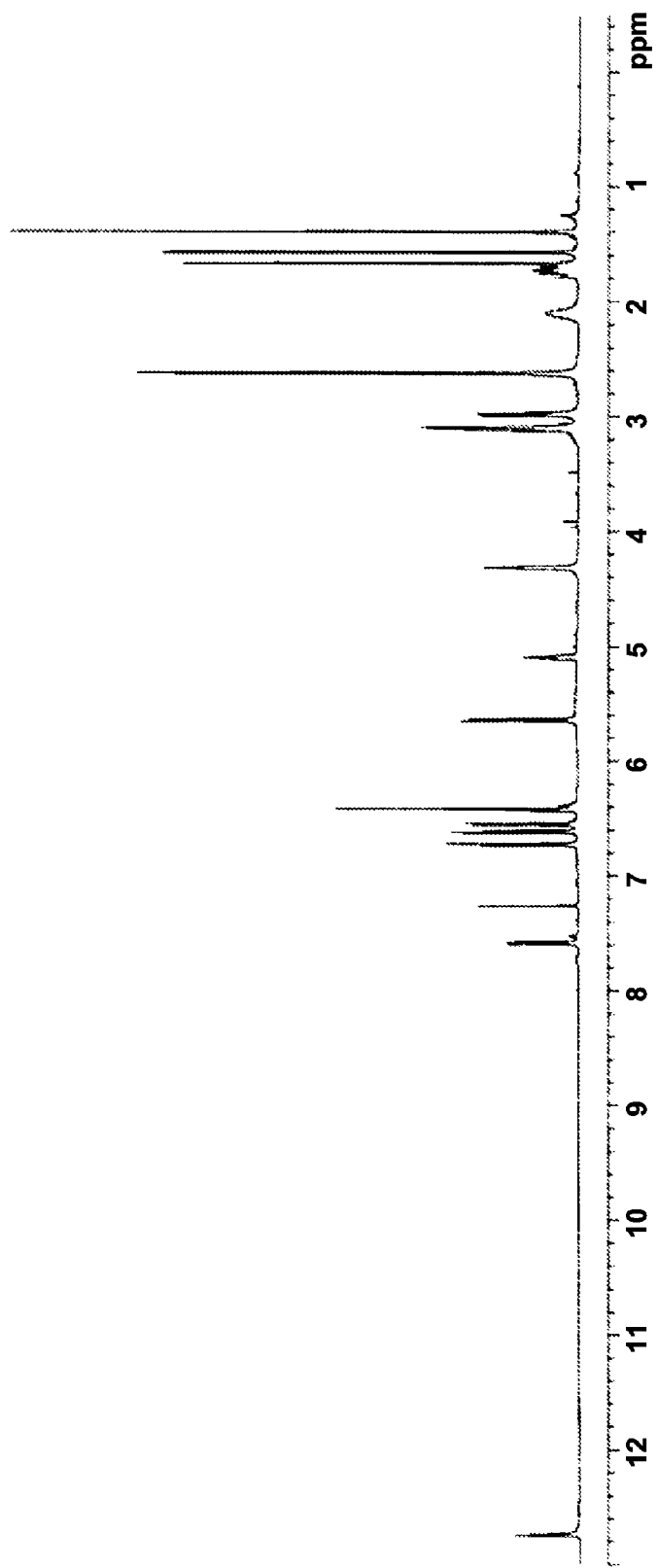
FIGS. 1a and 1b illustrate the hydrogen NMR spectrum to investigate the molecular structure of the geranyl flavonoid derivative prepared in this invention.

The terms of the present invention are illustrated hereinafter.

The term "anticancer" used in this invention indicates the action to inhibit tumor cell growth or to kill cancer cells, suggesting that it includes all the actions for the prevention and treatment of cancer.

The term "prevention" used in this invention indicates all the actions to inhibit the tumor formation or to delay the outbreak of cancer by administering the composition of the invention.

The term "treatment" used in this invention indicates all the actions to improve the symptoms of disease or change the course of disease favorably or beneficially by administering the composition of the invention.

The term "administration" used in this invention indicates the action to provide a required material to a patient via a random but properly selected method.

The term "patient" used in this invention indicates human or animals such as monkey, dog, goat, pig, or rat with disease whose symptoms can be improved by the administration of the composition of the invention.

The term "pharmaceutically effective dose" used in this invention indicates the amount of applicable, reasonable or risky concentration enough to treat the disease.

The term "alkoxy" used in this invention indicates $C_1$-$C_3$ lower alkoxy group, which is exemplified by methoxy, ethoxy, propoxy, etc.

The term "alkyl" used in this invention indicates $C_1$-$C_4$ straight or branched radical, which is exemplified by methyl, ethyl, n-propyl, iso-propyl, n-butyl, iso-butyl, tert-butyl, etc.

The term "heterocyclic" used in this invention indicates 6-membered ring that has one or two heteroatoms selected from the group consisting of O and N, wherein aromatic ring is excluded. For example, piperazine and morpholine are included and particularly piperazine is preferred in this invention.

The term "heteroaryl" used in this invention indicates $C_4$-$C_{10}$ mono- or poly-cyclic aromatic ring having N as a heteroatom, which is exemplified by picolyl, pyridine, pyrimidine, pyrazine, and pyridazine. Among these, picolyl group is preferred in this invention.

The term "aryl" used in this invention indicates $C_6$-$C_{10}$ mono- or poly-cyclic aromatic ring, which is exemplified by phenyl and naphthyl, and particularly phenyl group is preferred in this invention.

The term "leaving group" used in this invention indicates halogen atom such as chlorine, bromine, and iodine, and toluenesulfonyloxy group and methanesulfonyloxy group.

Hereinafter, the present invention is described in detail.

The present invention provides the geranyl flavonoid derivative represented by the below formula 1 or the pharmaceutically acceptable salt thereof:

[Formula 1]

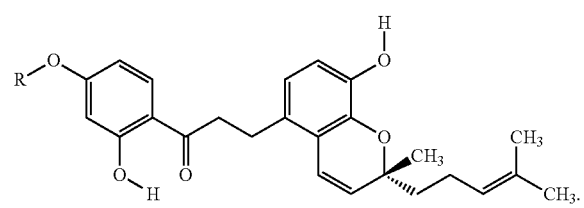

In the formula 1, R is preferably selected from the group consisting of a $C_{1-3}$ linear or branched chain alkoxy group; a $C_{1-4}$ linear or branched chain alkyl carbonyl group; a substituted or unsubstituted 6-membered heterocycloalkyl carbonyl group comprising one or two heteroatoms selected from the group consisting of O and N; a substituted or unsubstituted $C_{4-10}$ heteroaryl comprising one or more Ns; a substituted or unsubstituted $C_{6-10}$ aryl sulfonyl; or a dimethylamino $C_{1-3}$ linear or branched chain alkyl, wherein the substituted 6 membered heterocycloalkyl, substituted $C_{4-10}$ heteroaryl and substituted $C_{6-10}$ aryl may be independently substituted by one or more $C_{1-4}$ linear or branched alkyl, more specifically N,N-dimethylaminoethyl group is preferred, but not always limited thereto.

The geranyl flavonoid derivative herein is preferably the compound represented by formula 2 or formula 3, but not always limited thereto.

[Formula 2]

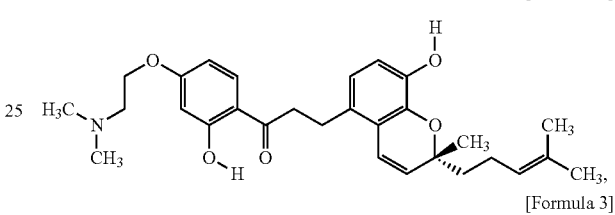

[Formula 3]

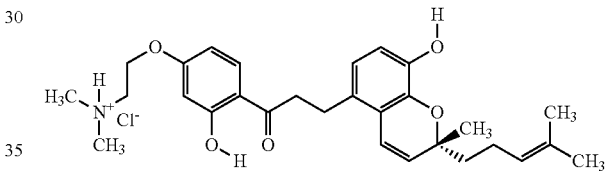

The geranyl flavonoid derivative represented by formula 1 of the present invention can be used as the form of a pharmaceutically acceptable salt, in which the salt is preferably acid addition salt formed by pharmaceutically acceptable free acids. Herein, the pharmaceutically acceptable salt indicates any organic or inorganic addition salt of the compound represented by formula 1 that is relatively non-toxic to a patient and has non-harmful activity whose side effect cannot reduce any positive effect of the said compound represented by formula 1.

Whether it is inorganic or organic, a free acid can be used if it is pharmaceutically acceptable. Examples of the inorganic free acid include hydrochloric acid, bromic acid, nitric acid, sulfuric acid, perchloric acid, and phosphoric acid. Available organic free acids are exemplified by citric acid, acetic acid, lactic acid, malic acid, fumaric acid, gluconic acid, succinic acid, tartaric acid, galacturonic acid, embonic acid, glutamic acid, aspartic acid, oxalic acid, (D) or (L) malic acid, maleic acid, methanesulfonic acid, ethanesulfonic acid, 4-toluenesulfonic acid, salicylic acid, citric acid, benzoic acid, and malonic acid.

The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxy-benzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, β-hydroxybutylate, glycolate, malate, tartrate, methanesulfonate, propanesulfonate, naphthalene-1-sulfonate, naphthalene-2-sulfonate and mandelate.

The acid addition salt in this invention can be prepared by the conventional method known to those in the art. For example, the geranyl flavonoid derivative of the present invention is dissolved in water-miscible organic solvent such as methanol, ethanol, acetone, or acetonitrile, to which excessive organic acid or acid aqueous solution of inorganic acid is added in order to induce precipitation or crystallization. Then, the solvent or the excessive acid is evaporated from the mixture, followed by drying the mixture to give addition salt or suction-filtering the precipitated salt to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The geranyl flavonoid derivative of the present invention includes not only a pharmaceutically acceptable salt thereof but also a salt, a hydrate, and a solvate possibly produced from the same.

The addition salt in this invention can be prepared by the conventional method known to those in the art. For example, the geranyl flavonoid derivative of the present invention is dissolved in water-miscible organic solvent such as methanol, ethanol, acetone, or acetonitrile, to which excessive organic acid or acid aqueous solution of inorganic acid is added in order to induce precipitation or crystallization. Then, the solvent or the excessive acid is evaporated from the mixture, followed by drying the mixture to give addition salt or suction-filtering the precipitated salt to give the same.

The present invention also provides a method for preparing the flavonoid derivative containing the step of preparing a geranyl flavonoid derivative by reacting the hydroxy geranyl flavonoid represented by formula 4, in the presence of a reaction solvent, with the substituted dimethyl aminoethyl chloride compound represented by formula 5 in the presence of a carbonate compound.

[Reaction Formula 1]

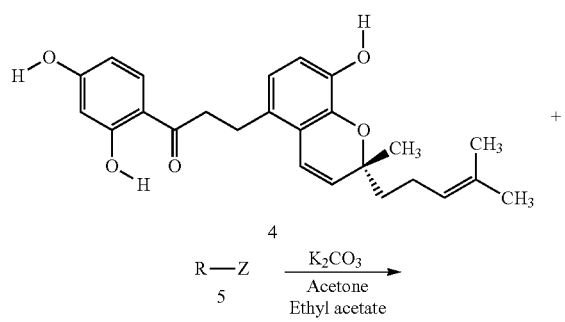

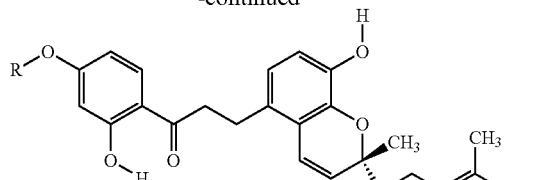

[Formula 4]

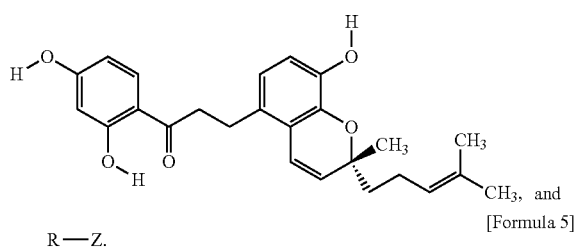

[Formula 5]

R—Z.

In the reaction formula 1, R is preferably selected from the group consisting of $C_1$-$C_3$ alkoxy group, $C_1$-$C_4$ alkylcarbonyl group; 6-membered heterocyclic carbonyl group unsubstituted or substituted with one or more $C_1$-$C_4$ alkyl groups, and having one or two heteroatoms selected from the group consisting of O and N; $C_4$-$C_{10}$ heteroaryl group having one or two Ns as heteroatoms; and sulfonyl group substituted with $C_6$-$C_{10}$ aryl group, more specifically N,N-dimethylaminoethyl group is preferred, but not always limited thereto.

In the reaction formula 1, R is preferably a leaving group and more preferably Cl or Br, but not always limited thereto.

The reaction is preferably performed in the presence of a carbonate compound for 5~20 hours, and more preferably for 10 hours, but not always limited thereto.

The organic solvent used herein is preferably ethylacetate, acetonitrile, or acetone, and more preferably acetonitrile or acetone.

In the method for preparing the geranyl flavonoid derivative, the step of dissolving the prepared geranyl flavonoid derivative in an organic solvent such as acetone and then reacting thereof in the presence of HCl can be additionally included. At this time, the geranyl flavonoid derivative prepared by the method including such an additional step displays more improved water-solubility.

To analyze the structure of the geranyl flavonoid derivative of the present invention, UV spectrophotometry, IR (infrared) spectrophotometry, and high-resolution mass spectrometry were performed to determine the molecular weight and molecular formula of the purified compound. $^1$H or $^{13}$C-NMR spectrum was also obtained by using NMR (Varian 300 MHz, 500 MHz NMR). The structure was determined by analyzing the obtained spectrum.

The present invention also provides a method for treating cancer containing the step of administering a pharmaceutically effective dose of the geranyl flavonoid derivative represented by formula 1 or a pharmaceutically acceptable salt thereof to a subject.

The said geranyl flavonoid derivative is preferably the compound represented by formula 2 or formula 3, but not always limited thereto.

The geranyl flavonoid derivative is preferably to inhibit the expression of a STAT3 target protein by inhibiting the phosphorylation of STAT3 (Signal Transducers and Activators of Transcription 3) protein, but not always limited thereto.

The cancer herein is preferably selected from the group consisting of colon cancer, lung cancer, non-small cell lung cancer, bone cancer, pancreatic cancer, skin cancer, head & neck cancer, skin melanoma, choroidal melanoma, uterine cancer, ovarian cancer, rectal cancer, stomach cancer, anal cancer, colon cancer, breast cancer, fallopian tube carcinoma, endometrial carcinoma, uterine cervical carcinoma, vaginal carcinoma, vulval carcinoma, Hodgkin's disease, esophageal cancer, small bowel cancer, endocrine cancer, thyroid cancer, parathyroid cancer, adrenal cancer, soft tissue sarcoma, urethral cancer, penis cancer, prostate cancer, chronic leukemia, acute leukemia, lymphoma, bladder cancer, kidney cancer, ureter cancer, renal cell carcinoma, renal pelvic carcinoma, and CNS (central nervous system) tumor, and more preferably is prostate cancer, but not always limited thereto.

Figure 1B:
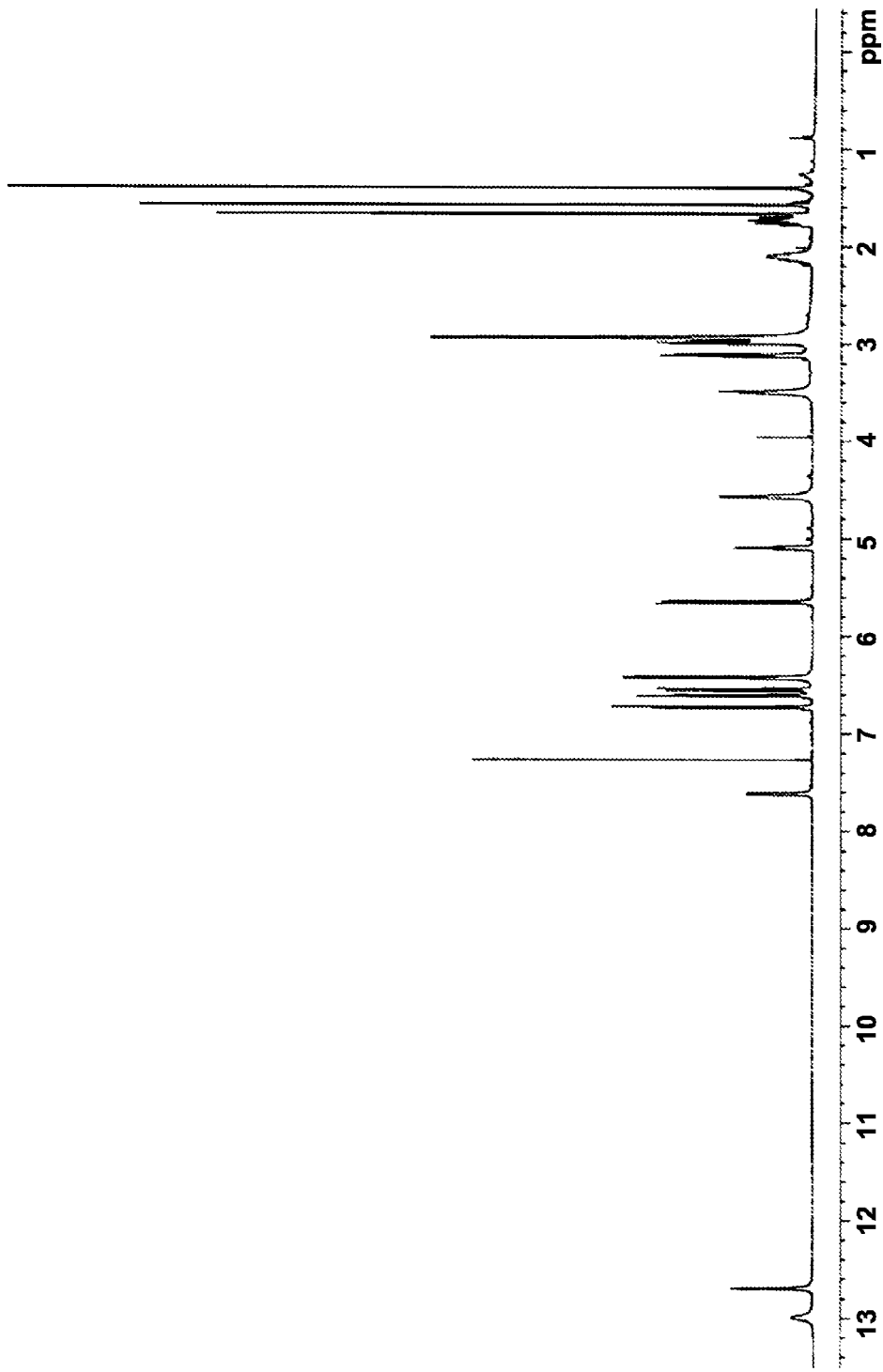
Figure 2:
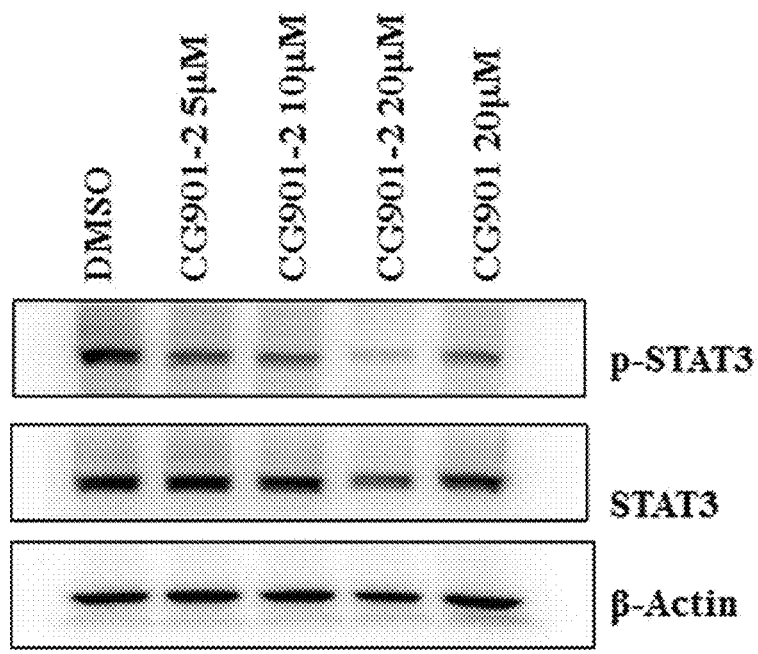
FIG. 2 is a diagram illustrating the result of Western blotting performed to investigate the expression and the phosphorylation of STAT3 by the geranyl flavonoid derivative of the invention.

In a preferred embodiment of the present invention, hydroxy geranyl flavonoid was organically synthesized, from which the novel geranyl flavonoid derivatives, (R)-1-(4-(2-(dimethylamino)ethoxy)-2-hydroxyphenyl)-3-(8-hydroxy-2-methyl-2-(4-methylpent-3-enyl)-2H-chromen-5-yl)propan-1-one and (R)-2-(3-hydroxy-4-(3-(8-hydroxy-2-methyl-2-(4-methylpent-3-enyl)-2H-chromen-5-yl)propanoyl)phenoxy)-N,N-dimethylethanaminium chloride, with improved water-solubility were synthesized and named respectively CG-901-1 and CG-901-2 (see FIG. 1, FIG. 2, Table 1, and Table 2).

The present inventors investigated the STAT3 (Signal Transducers and Activators of Transcription 3) protein activity inhibiting effect of the geranyl flavonoid derivative CG-901-2 prepared in this invention. As a result, the said CG-901-2 reduced the phosphorylation level of the STAT3 protein and inhibited the expression of such STAT3 target proteins as cycline A, Mcl-1 (Induced myeloid leukemia cell differentiation protein-1), and survivine (see FIGS. 2 and 3), and accordingly displayed cancer cell growth inhibiting effect in various cancer cell lines (see Table 3).

In addition, the present inventors investigated in vivo anti-cancer effect of the geranyl flavonoid derivative CG-901-2 prepared in this invention. To do so, the mouse model transplanted with prostate cancer was orally administered with the geranyl flavonoid derivative CG-901-2. As a result, in the mouse model treated with the geranyl flavonoid derivative CG-901-2 at the concentration of 50 mg/kg for 10 days, the size and the weight of tumor was reduced (see FIG. 4).

Therefore, the novel geranyl flavonoid derivative of the present invention has the improved water-solubility and can inhibit STAT3 protein activity, suggesting that it displays cancer cell growth inhibiting effect in vivo and in vitro, so that it can be effectively used for the method for treating cancer.

When the geranyl flavonoid derivative or the pharmaceutically acceptable salt thereof of the present invention is used as a medicine, the pharmaceutical composition comprising the geranyl flavonoid derivative or the pharmaceutically acceptable salt thereof as an active ingredient can be formulated in diverse formulations clinically suitable for oral or parenteral administration, as shown below, but not always limited thereto.

The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavors, and sweeteners can be additionally included thereto.

The pharmaceutical composition comprising the geranyl flavonoid derivative or the pharmaceutically acceptable salt thereof of the present invention as an active ingredient can be administered by parenterally and the parenteral administration includes subcutaneous injection, intravenous injection, intramuscular injection and intrathoracic injection. To prepare the pharmaceutical composition comprising the geranyl flavonoid derivative or the pharmaceutically acceptable salt thereof as an active ingredient as a formulation for parenteral administration, the geranyl flavonoid derivative or the pharmaceutically acceptable salt thereof is mixed with a stabilizer or a buffering agent to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The effective dosage of the geranyl flavonoid derivative or the pharmaceutically acceptable salt thereof of the present invention can be adjusted according to the age, weight, and gender of patient, administration pathway, health condition, severity of disease, etc. For example, the dosage for an adult patient in body weight of 60 kg is generally 0.001~1,000 mg/day, and preferably 0.01~500 mg/day, which can be administered once a day or the dosage can be divided and administered several times a day at a regular interval according to the judgment of a doctor or a pharmacist.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Geranyl Flavonoid Derivative

<1-1> Preparation of the Geranyl Flavonoid Derivative Compound CG-901-1

The geranyl flavonoid derivative was prepared and the physicochemical properties thereof was investigated by performing UV spectrophotometry, IR (infrared) spectrophotometry, and high-resolution mass spectrometry. As a result, the molecular weight and the molecular formula of the purified compound were determined.

Particularly, 1 g of hydroxy geranyl flavonoid was dissolved in 200 ml of acetone, to which 2 g of potassium carbonate and 0.8 g of N,N-dimethylethyl amine chloride were added, followed by stirring at room temperature for 10 hours. Upon completion of the reaction, the organic solvent layer comprising active compounds was concentrated under reduced pressure. The concentrated extract was obtained. 1.1 g of the concentrated extract was dissolved in 30 ml of methylene chloride. Active fractions were separated by silica gel column chromatography (Art No. 9385, Merck) using the mixed solvent of ethyl acetate and hexane (50:50 (v/v)). As a result, 800 mg of the light yellow geranyl flavonoid derivative compound was obtained (yield: 70%).

UV spectrophotometry was performed with the obtained compound using UV-265 spectrophotometer (Shimadzu, Japan). IR spectrophotometry was performed using Digilab Division FTS-80 spectrophotometer (Bio-Rad). The molecular weight and the molecular formula of the compound were determined by High resolution MS using VG70-SEQ mass spectrometry (MS). $^1$H or $^{13}$C-NMR spectrum was obtained by using Varian 300 MHz, 500 MHz NMR. The final structure was determined by analyzing the obtained spectrum.

As a result, as shown in FIG. 1a and Table 1, it was confirmed that (R)-1-(4-(2-(dimethylamino)ethoxy)-2-hydroxyphenyl)-3-(8-hydroxy-2-methyl-2-(4-methylpent-3-enyl)-2H-chromen-5-yl)propan-1-one having the structure of formula 2 was synthesized, which was named CG-901-1. The physicochemical properties of the synthesized compound were confirmed (FIG. 1a).

[Formula 2]

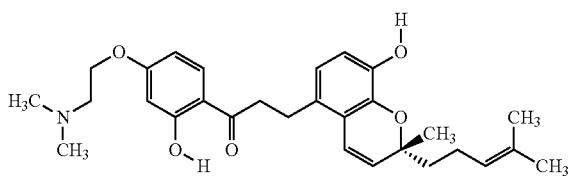

TABLE 1

| Appearance | Light Yellow |
| --- | --- |
| Molecular Formula | $C_{29}H_{37}NO_5$ |
| MW | 479.53 |
| Melting Point (° C.) | Oil |
| Solubility    Fusibility | Alcohol, DMSO |
|               Insolubility | Hexane |
|               Water-solubility | 300M |

$^1$H-NMR (CDCl3): 12.74 (1H, s), 7.58 (1H, d, J=9.5), 7.26 (1H, s), 6.72 (1H, d, J=8.5), 6.61 (1H, d, J=8.5), 6.55 (1H, d, J=9.5), 6.42 (1H, m), 6.40 (1H, s), 5.64 (1H, d, J=10.5), 5.09 (1H, m), 4.25 (2H, m), 3.10 (4H, m), 2.97 (2H, m), 2.62 (6H, s), 2.10 (2H, m), 1.75 (2H, m), 1.66 (3H, s), 1.57 (3H, s), 1.39 (3H, s).

<1-2> Preparation of the Geranyl Flavonoid Derivative Compound CG-901-2 of Formula 3

1 g of the compound of formula 2 prepared in Example <1-1> was dissolved in 200 ml of acetone, to which 1 ml of 37% HCl was added, followed by reaction with stirring for 1 hour. Upon completion of the reaction, the organic solvent layer containing the active material was concentrated under reduced pressure. The concentrated extract was re-crystallized to give 1 g of the compound of formula 3, which was named CG-901-2. The physicochemical properties of the obtained compound CG-901-2 were confirmed by the same manner as described in Example <1-1>.

As a result, as shown in FIG. 1b and Table 2, it was confirmed that (R)-2-(3-hydroxy-4-(3-(8-hydroxy-2-methyl-2-(4-methylpent-3-enyl)-2H-chromen-5-yl)propanoyl)phenoxy)-N,N-dimethylethanaminium chloride having the structure of formula 3 was synthesized, which was named CG-901-2. The physicochemical properties of the synthesized compound were confirmed (FIG. 1b).

[Formula 3]

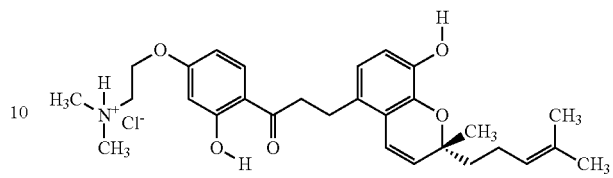

TABLE 2

| Appearance | Light Yellow |
| --- | --- |
| Molecular Formula | $C_{29}H_{38}ClNO_5$ |
| MW | 515.98 |
| Melting Point (° C.) | 80 |
| Solubility    Fusibility | Alcohol, $H_2O$ |
|               Insolubility | Hexane, Ethylacetate |

$^1$H-NMR (CDCl3): 12.98 (1H, s), 12.69 (1H, s), 7.61 (1H, d, J=8.0), 7.26 (1H, s), 6.72 (1H, d, J=8.5), 6.60 (1H, d, J=8.5), 6.54 (1H, d, J=9.5), 6.42 (1H, m), 6.41 (2H, s), 5.64 (1H, d, J=9.5), 5.09 (1H, m), 4.56 (2H, s), 3.48 (2H m), 3.11 (2H, m), 2.97 (2H, m), 2.93 (6H, s), 2.10 (2H, m), 1.73 (2H, m), 1.66 (3H, s), 1.57 (3H, s), 1.39 (3H, s).

Example 2

Inhibitory Effect of Geranyl Flavonoid Derivative on the Activity of STAT3

<2-1> Inhibitory Effect of Geranyl Flavonoid Derivative on the Phosphorylation of STAT3

To investigate whether or not the novel synthesized geranyl flavonoid derivative of the present invention, CG-901-2, had the activity of inhibiting STAT3 protein activity by inhibiting STAT3 phosphorylation, Western blotting was performed to measure the expression of the phosphorylated STAT3.

Particularly, the prostate cancer cell line DU-145 was distributed in three 60-mm plates containing 10% FBS (fetal bovine serum) medium at the density of 80,000 cells/plate, followed by culture in a 37° C. 5% $CO_2$ incubator for 24 hours. Upon completion of the culture, the CG-901-2 compound prepared in Example <1-2> was treated to each plate at the concentration of 5, 10, or 20 μM. The negative control was treated with 0.25% DMSO, followed by culture for 24 hours. Then, the medium was discarded from each plate. The plate was then washed with PBS, to which 200 μl of Ripa lysis buffer was added. The cells attached on the plate were collected by using a scraper. The collected cells were transferred into a 1.5 ml tube, followed by centrifugation at 4° C., 13,000 rpm, for 15~30 minutes to obtain supernatant containing cell lysate. The obtained lysate was transferred into a new 1.5 ml tube. 80 μl of D.W. 10 μl of lysate, and 200 μl of Bradford assay reagent were mixed in the tube, followed by vortexing. The lysate mixture was placed in a 96-well plate, and $OD_{959}$ was measured using ELISA reader in order to quantify the protein.

After the quantification, the lysate containing the equal amount of protein was prepared, which was mixed with lysis buffer and 5× dye, leading to the preparation of a loading sample. The sample was heated at 80° C. for 10 minutes to inactive the protein. The inactivated protein was loaded on acrylamide sodium dodecyl sulfate (SDS) gel, followed by transferring at 0.25 A for 2 hours. The transferred/separated protein was transferred onto a membrane. The transferred protein was blocked with skim milk for 1 hour. The membrane was then conjugated with the primary antibody, anti-phosphorylated-STAT3 antibody (Cell Signaling Technology), followed by further reaction with the secondary antibody (Cell Signaling Technology) for 1 hour. Substrate was sprayed on the membrane, followed by measuring chemoluminescence by using LAS image analyzer in order to measure the expression of p-STAT3.

As a result, as shown in FIG. 2, the expression of STAT3 was not changed but the phosphorylation of STAT3 was reduced CG-901-2 dose-dependently. That is, the treatment of the geranyl flavonoid derivative resulted in the decrease of STAT3 phosphorylation and accordingly the inhibition of STAT3 protein activity (FIG. 2).

<2-2> Changes in Gene Expression According to the Inhibition of STAT3 Phosphorylation To investigate the changes of the expression of STAT3 target genes according to the decrease of STAT3 protein phosphorylation caused by the treatment of geranyl flavonoid derivative CG901-2, the expressions of cyclin A that is well known as a STAT3 target protein, Mcl-1 (Induced myeloid leukemia cell differentiation protein-1), and survivin were examined.

Particularly, DU-145 cells were treated with the compound CG-901-2 at the concentration of 20 µM by the same manner as described in Example <2-1>, followed by culture. Western blotting was performed to investigate the expressions of AD (cyclin A), Mcl-1, and survivin. β-actin was used as the control to compare the expression levels.

Figure 3:
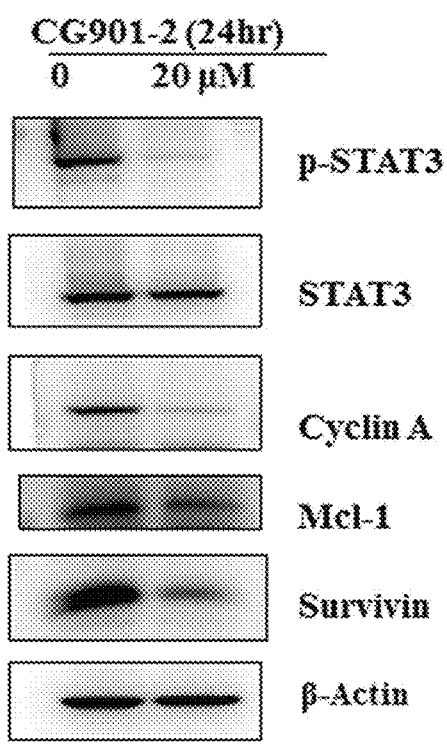
FIG. 3 is a diagram illustrating the decrease of the STAT3 target protein expression by the geranyl flavonoid derivative of the invention.

As a result, as shown in FIG. 3, when CG-901-2 was treated to the prostate cancer cell line, the STAT3 target proteins cyclin A, Mcl-1, and survivine were all down-regulated (FIG. 3).

Example 3

Cancer Cell Growth Inhibiting Effect of Geranyl Flavonoid Derivative

To investigate whether or not the geranyl flavonoid derivative of the present invention had cancer cell growth inhibiting effect, various human cancer cell lines were treated with CG-901-2 and then cancer cell growth was observed.

Particularly, the human breast cancer cell lines MDA-MB-231 and MDA-MB-468, the prostate cancer cell line DU-145, the colorectal cancer cell line HCT116, the pancreatic cancer cell line AsPC-3, or the colon cancer cell line SW620 was distributed in 10% FBS medium, followed by culture in a 37° C. 5% $CO_2$ incubator. The attached grown cells were collected by using trypsin-EDTA. The obtained cells were counted by hematocytometer, which were distributed in 96-well plate at the density of 5,000 cells/well (MDA-MB-231, MDA-MB-468, and DU-145) or at the density of 7,000 cells/well (HCT116 and SW620). 10% FBS medium was added to the plate, followed by culture in a 37° C. 5% $CO_2$ incubator. 24 hours later, the cells were treated with the compound CG-901-2 prepared in Example <1-2> dissolved in DMSO at the concentration of 20 or 50 µg/ml. The negative control was treated with 0.1% DMSO. The cells were further cultured for 24 more hours. Then, 10 µl of the coloring agent, 2-[4-iodophenyl]-3-[4-nitrophenyl]-5-[2,4-disulfophenyl]-2H-tetrazolium (monosodium salt, WST-1; Roche) was treated to the cultured cells, followed by culture for 2 hours. Then, $OD_{450}$ was measured with ELISA reader (Bio-Rad) to investigate the time-dependent cancer cell growth rate. For 24 hours from the treatment of the compound, the concentration of the compound that allowed only 50% of cancer cell population to survive was calculated based on the above growth rate, and the result was defined as $GI_{50}$.

As a result, as shown in Table 3, when the breast cancer cell lines MDA-MB-231 and MDA-MB-468, the prostate cancer cell line DU-145, the colorectal cancer cell line HCT116, the pancreatic cancer cell line AsPC-3, or the colon cancer cell line SW620 was treated with the compound CG-901-2, the cancer cell growth rate was reduced over the time, compared with that of the negative control. Each cancer cell line displayed $GI_{50}$ in the concentration range of 15~30 µM (Table 3).

TABLE 3

$GI_{50}$ of geranyl flavonoid derivative CG-901-2

| Cancer cell line | | |
| --- | --- | --- |
| Origin | Name | $GI_{50}$ (µM) |
| Prostate cancer | DE-146 | 20 |
| Colorectal cancer | HCT116 | 25 |
| Breast cancer | MDA-MB-468 | 30 |
| Colon cancer | SW620 | 50 |

Example 4

In Vivo Anticancer Effect of Geranyl Flavonoid Derivative

<4-1> Construction of the Prostate Cancer Mouse Model

To investigate whether or not the geranyl flavonoid derivative of the present invention had a significant anticancer-effect, the prostate cancer mouse model was constructed.

Particularly, the human originated prostate cancer cell line DU-145 was inoculated in the serum-free medium, followed by culture in a 37° C. 5% $CO_2$ incubator. The cultured DU-145 cells were prepared at the density of $3 \times 10^7$ cells/ml. Each BALB/c specific pathogen free female mouse (Nara Biotech Co.) at 6 weeks was administered with the cells at the dose of $9 \times 10^6$ cells/0.3 ml via subcutaneous injection in the auxiliary region between the right shoulder and breast wall, leading to the cancer cell transplantation. After the transplantation, the mouse was raised for 25 days until the generated tumor induced by the transplanted cancer cells grew to a measurable size. As a result, the prostate cancer mouse model was constructed.

The tumor induced by the transplanted cancer cells was measured in three dimensions which were length, width, and height of the tumor, by using a vernier caliper, total 7 times, and the size of the tumor was calculated by the below mathematical formula 1.

Tumor Size=length×width×height of tumor/2      [Mathematical Formula 1]

<4-2> In Vivo Tumor Size Inhibiting Effect of Geranyl Flavonoid Derivative

To investigate whether or not the geranyl flavonoid derivative of the present invention had a significant in vivo anticancer effect, the present inventors treated the prostate cancer mouse model with CG-901-2, and then observed the changes of the tumor growth.

Particularly, the compound CG-901-2 prepared in Example <1-2> was dissolved in sterilized distilled water at the concentration of 5 mg/ml. The prepared compound was orally administered to the prostate cancer mouse model constructed in Example <4-1> at the concentration of 0.2 ml/20 g of body weight (10 ml/1 kg weight). The oral administration was performed from the next day of the cancer cell transplantation (day 1), once a day, for 10 times total. The tumor size was measured on day 0, day 10, day 14, day 16, day 18, day 21, day 23, and day 25. 25 days after the oral administration began, the mouse was sacrificed with $CO_2$ and the tumor was separated and weighed. For the negative control, the prostate cancer mouse model prepared by the same manner as described above was treated with sterilized distilled water alone and the mouse was raised under the same condition. The size and weight of the control tumor was measured and compared with the above.

Figure 4:
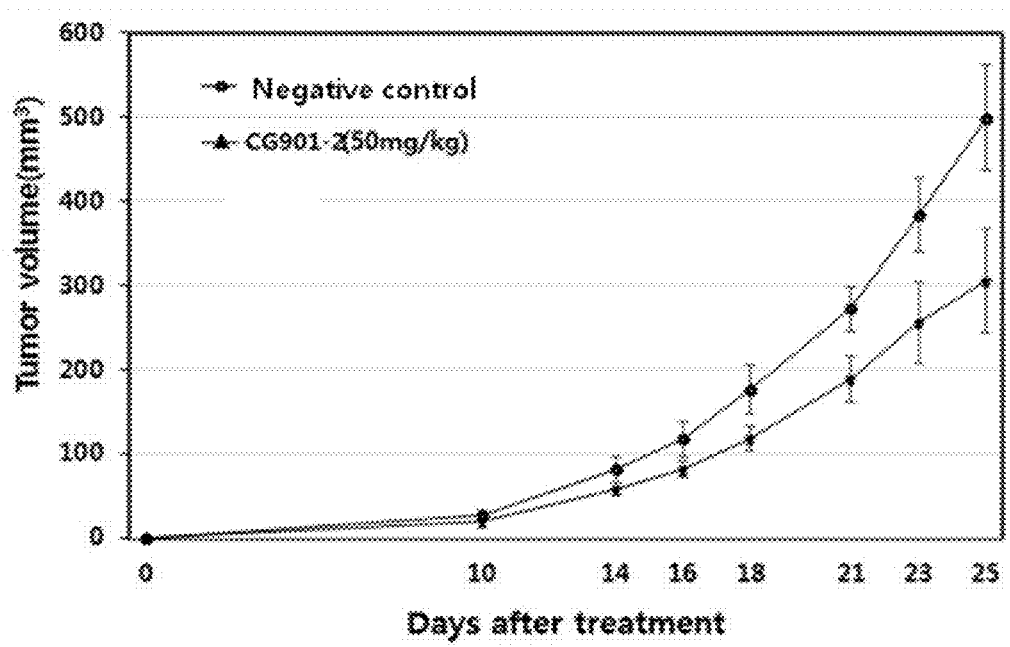
FIG. 4 is a diagram illustrating the inhibition of tumor size growth in vivo by the geranyl flavonoid derivative of the invention.

As a result, as shown in FIG. 4, the tumor size growth was approximately 38.8% inhibited in the mouse group treated with CG-901-2 at the concentration of 50 mg/kg, compared with that of the negative control mouse. The weight of the tumor was also 40.5% reduced. The above result indicates that the compound of the present invention had a statistically significant anticancer effect ($p<0.001$) (FIG. 4).

Manufacturing Example 1

Preparation of Pharmaceutical Formulations

<1-1> Preparation of Powders

The compound of the present invention or the pharmaceutically acceptable salt thereof 0.1 g
Lactose 1.5 g
Talc 0.5 g Powders were prepared by mixing all the above components, which were filled in airtight packs according to the conventional method for preparing powders.

<1-2> Preparation of Tablets

The compound of the present invention or the pharmaceutically acceptable salt thereof 0.1 g
Lactose 7.9 g
Cellulose, crystalline 1.5 g
Magnesium stearate 0.5 g Tablets were prepared by mixing all the above components by direct tableting method.

<1-3> Preparation of Capsules

The compound of the present invention or the pharmaceutically acceptable salt thereof 0.1 g
Corn starch 5 g
Carboxy cellulose 4.9 g Capsules were prepared by mixing all the above components, which were filled in hard capsules according to the conventional method for preparing capsules.

<1-4> Preparation of Injectable Solutions

The compound of the present invention or the pharmaceutically acceptable salt thereof 0.1 g
Sterilized distilled water for injection proper amount
pH regulator proper amount Injectable solutions were prepared by mixing all the above components, putting the mixture into 2 ml ampoules and sterilizing thereof by the conventional method for preparing injectable solutions.

<1-5> Preparation of Liquid Formulations

The compound of the present invention or the pharmaceutically acceptable salt thereof 0.1 g
Isomerized sugar 10 g
Mannitol 5 g
Purified water proper amount All the above components were dissolved in purified water. After adding lemon flavor, total volume was adjusted to be 100 ml by adding purified water. Liquid formulations were prepared by putting the mixture into brown bottles and sterilizing thereof by the conventional method for preparing liquid formulations.

INDUSTRIAL APPLICABILITY

The novel geranyl flavonoid derivative of the present invention or the pharmaceutically acceptable salt thereof inhibits STAT3 activity in cancer cells which results in the inhibition of abnormal growth of tumor cells and also displays improved water-solubility which favors increasing anticancer effect. Therefore, the geranyl flavonoid derivative of the invention or the pharmaceutically acceptable salt thereof can be efficiently used for the treatment of cancer.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A geranyl flavonoid derivative represented by Formula 2 or a pharmaceutically acceptable salt thereof.

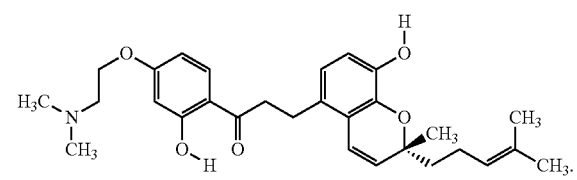

[Formula 2]

2. The geranyl flavonoid derivative or the pharmaceutically acceptable salt thereof according to claim 1, wherein the pharmaceutically acceptable salt thereof is the compound represented by Formula 3:

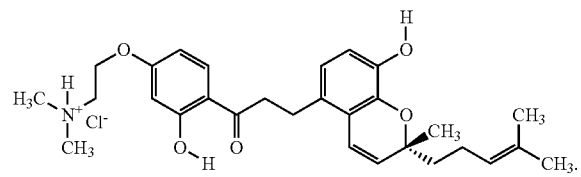

[Formula 3]

3. A method for preparing the flavonoid derivative of claim 1 comprising the step of preparing a geranyl flavonoid derivative by reacting hydroxy geranyl flavonoid (4), in the presence of a reaction solvent, with dimethyl aminoethyl chloride (5) substituted in the presence of a carbonate compound:

[Reaction Formula 1]

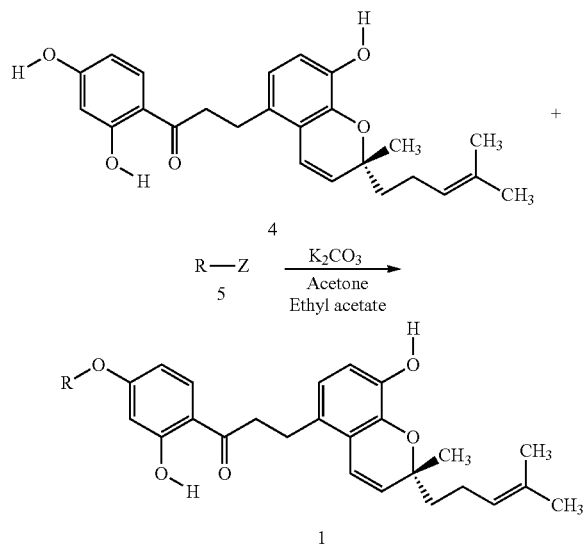

wherein, R is N,N-dimethyl aminoethyl; and Z is chloride as a leaving group.

4. A method for preparing the pharmaceutically acceptable salt Formula 3

[Formula 3]

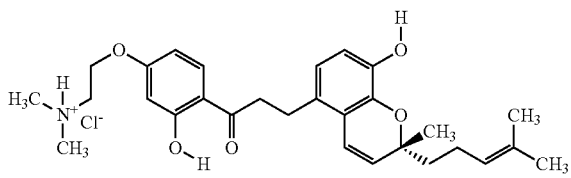

comprising the step of, dissolving the geranyl flavonoid derivative of claim 1 in an organic solvent and then reacting the flavonoid derivative of claim 1 in the presence of HCl.

5. A method for treating cancer in a subject comprising administering a therapeutically effective amount of the geranyl flavonoid derivative of claim 1 to the subject.

6. The method according to claim 5, wherein the geranyl flavonoid derivative inhibits the phosphorylation of STAT3 (Signal Transducers and Activators of Transcription 3) protein.

7. The method according to claim 5, wherein the cancer is one or more cancers selected from the group consisting of colon cancer, lung cancer, non-small cell lung cancer, bone cancer, pancreatic cancer, skin cancer, head & neck cancer, skin melanoma, choroidal melanoma, uterine cancer, ovarian cancer, rectal cancer, stomach cancer, anal cancer, colon cancer, breast cancer, fallopian tube carcinoma, endometrial carcinoma, uterine cervical carcinoma, vaginal carcinoma, vulval carcinoma, Hodgkin's disease, esophageal cancer, small bowel cancer, endocrine cancer, thyroid cancer, parathyroid cancer, adrenal cancer, soft tissue sarcoma, urethral cancer, penis cancer, prostate cancer, chronic leukemia, acute leukemia, lymphoma, bladder cancer, kidney cancer, ureter cancer, renal cell carcinoma, renal pelvic carcinoma, and CNS (central nervous system) tumor.

8. The method according to claim 5 wherein the cancer is a prostate, colorectal, breast or colon cancer.

9. A method of inhibiting phosphorylation of STAT3 (Signal Transducers and Activators of Transcription 3) protein in a subject by administering a therapeutically effective amount of the geranyl flavonoid derivative of claim 1 to the subject.

\* \* \* \* \*